United States Patent [19]
Rahim et al.

[11] Patent Number: 5,198,539
[45] Date of Patent: Mar. 30, 1993

[54] 5'-ESTERS OF 2',3'-DIDEOXY-3'-FLUORO-5-ETHYNYLURIDINE

[75] Inventors: Saad G. Rahim, Beckenham, England; Thomas A. Krenitsky, Chapel Hill, N.C.

[73] Assignee: Burroughs Wellcome Co., Research Triangle Park, N.C.

[21] Appl. No.: 745,323

[22] Filed: Aug. 15, 1991

Related U.S. Application Data

[63] Continuation of Ser. No. 394,987, Aug. 17, 1989, Pat. No. 5,157,114.

[30] Foreign Application Priority Data

Aug. 19, 1988 [GB] United Kingdom ............... 8819732.2
Jan. 20, 1989 [GB] United Kingdom ............... 8901294.2

[51] Int. Cl.$^5$ .................................... C07H 19/073
[52] U.S. Cl. .................... 536/26.26; 514/43; 514/50; 514/51; 536/26.21; 536/26.8; 536/28.2
[58] Field of Search ............ 514/50, 51; 536/23, 536/29

[56] References Cited

FOREIGN PATENT DOCUMENTS 0316017 5/1989 European Pat. Off. .
8808001 10/1988 PCT Int'l Appl. .

OTHER PUBLICATIONS

DeClercq, Meth. Find. Exptl. Clin. Pharmacol., 2(5), 253-267 (1980).

Primary Examiner—Johnnie R. Brown
Assistant Examiner—L. Eric Crane
Attorney, Agent, or Firm—Donald Brown; Lawrence A. Nielsen; Hannah O. Green

[57] ABSTRACT

The present invention relates to a 3'-substituted pyrimidine nucleoside and its use in medical therapy, particularly in the treatment of HIV infections. Also provided are pharmaceutical formulations.

5 Claims, No Drawings

5'-ESTERS OF 2',3'-DIDEOXY-3'-FLUORO-5-ETHYNYLURIDINE

This is a continuation of copending application(s) Ser. No. 07/394,987 filed on Aug. 17, 1989, U.S. Pat. No. 5,157,114.

The present invention relates to a certain 3'-fluoro nucleoside analogue, pharmaceutically acceptable derivatives thereof, and the use of such compounds in therapy, particularly for the treatment of certain viral infections.

One group of viruses which has recently assumed a particular importance are the retroviruses. Retroviruses form a sub-group of RNA viruses which, in order to replicate, must first 'reverse transcribe' the RNA of their genome into DNA ('transcription' conventionally describes the synthesis of RNA from DNA). Once in the form of DNA, the viral genome may be incorporated into the host cell genome, allowing it to take advantage of the host cell's transcription/translation machinery for the purposes of replication. Once incorporated, the viral DNA is virtually indistinguishable from the host's DNA and, in this state, the virus may persist for the life of the cell.

A species of retrovirus, Human Immunodeficiency Virus (HIV), has been reproducibly isolated from patients with Acquired Immune Deficiency Syndrome (AIDS) or with the symptoms that frequently precede AIDS. AIDS is an immunosuppressive or immunodestructive disease that predisposes subjects to fatal opportunistic infections. Characteristically, AIDS is associated with a progressive depletion of T-cells, especially the helper-inducer subset bearing the OKT$^4$ surface marker. HIV is cytopathic and appears to preferentially infect and destroy T-cells bearing the OKT$^4$ marker and it is now generally recognised that HIV is the etiological agent of AIDS.

Since the discovery that HIV is the etiological agent of AIDS, numerous proposals have been made for anti-HIV chemotherapeutic agents that may be effective in treating AIDS. Thus, for example, European Patent Specification No. 196185 describes 3'-azido-3'-deoxythymidine (which has the approved name zidovudine), its pharmaceutically acceptable derivatives and their use in the treatment of human retrovirus infections including AIDS and associated clinical conditions. Other nucleoside derivatives that have been suggested for the treatment of HIV infections include the 3'-fluoronucleosides described for example in European Patent Specification 254 268 and International Patent Specification 88/0050.

Another group of viral pathogens of major consequence worldwide are the hepatitis viruses, in particular hepatitis B virus (HBV). HBV is most common in Asian countries, and prevalent in sub-Saharan Africa. The virus is etiologically associated with primary hepatocellular carcinoma and is thought to cause 80% of the world's liver cancer. In the United States more than ten thousand people are hospitalised for HBV illness each year, and an average of 250 die with fulminant disease. The United States currently contains an estimated pool of 500,000-1 million infectious carriers. Chronic active hepatitis will develop in over 25% of carriers, and often progresses to cirrhosis. It is estimated that 5000 people die from HBV related cirrhosis each year in the USA, and that perhaps 1000 die from HBV-related liver cancer. Thus, there is a great need for effective antiviral agents, both to control the chronic infection and reduce progression to hepatocellular carcinoma.

Clinical effects of infection with HBV range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease as outlined above. In "Viral Infections of Humans" (second edition, Ed., Evans, A. S. (1982) Plenum Publishing Corporation, New York), Chapter 12 describes the etiology of viral hepatitis infections.

We have now surprisingly discovered that 2',3'-dideoxy-5-ethynyl-3'-fluorouridine as referred to below has potent activity against retroviruses such as HIV, as well as HBV.

According to the present invention therefore we provide the compound of formula (I):

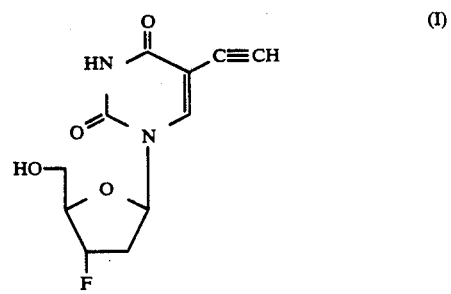

also characterised by the name 2',3'-dideoxy-5-ethynyl-3'-fluorouridine; and pharmaceutically acceptable derivatives thereof. Hereinafter the compound of formula (I) and its pharmaceutically acceptable derivatives will be referred to as compounds according to the invention.

Formula (I) above depicts the compound in the keto tautomeric form. It will be appreciated that the compound may also exist in the corresponding enol tautomeric form.

In a further aspect of the invention there are provided the compounds according to the invention for use in medical therapy particularly for the treatment of viral infections especially retroviral infections and hepatitis B viral infections in e.g. humans.

Examples of retroviral infections which may be treated in accordance with the invention include human retroviral infections such as HIV-1, HIV-2 and Human T-cell Lymphotropic Virus (HLTV) e.g. HTLV-I or HTLV-II infections.

The compounds according to the invention are also useful for the treatment of clinical conditions associated with retroviral infections, for example, AIDS, Kaposi's sarcoma, thrombocytopenic purpura, AIDS-related complex (ARC), progressive generalized lymphadenopathy (PGL), and patients carrying HIV-antibodies or who are seropositive to the HIV virus, as well as chronic neurological conditions such as multiple sclerosis or tropical spastic paraparesis.

The compounds according to the invention may also be used for the treatment of infections carried by DNA viruses which, like retroviruses, are incorporated into the host genome during their life-cycle, i.e. DNA viruses such as hepatitis B. Thus, there is further provided the compounds according to the invention for use in the treatment of infections caused by such retrovirus-like viruses.

In a further aspect of the present invention there is included:

a) A method for the treatment of a viral infection of a mammal including man which comprises treating the mammal with an antivirally effective amount of a compound according to the invention.

b) Use of a compound according to the invention in the manufacture of a medicament for the treatment of any of the above-mentioned infections or indications.

By "a pharmaceutically acceptable derivative" is meant any pharmaceutically acceptable salt, ester, or salt of such ester, of the compound of formula (I) or any other compound which, upon administration to the recipient, is capable of providing (directly or indirectly) such a compound or an antivirally active metabolite or residue thereof.

Preferred esters of the compound of formula (I) include carboxylic acid esters in which the non-carbonyl moiety of the ester grouping is selected from straight or branched chain alkyl (e.g. methyl, n-propyl, n-butyl or t-butyl), alkoxyalkyl (e.g. methoxymethyl), aralkyl (e.g. benzyl), aryloxyalkyl (e.g. phenoxymethyl), aryl (e.g. phenyl optionally substituted by halogen, $C_{1-4}$ alkyl or $C_{1-4}$ alkoxy or amino); sulphonate esters such as alkyl- or aralkylsulphonyl (e.g. methanesulphonyl); amino acid esters (e.g. L-valyl or L-isoleucyl); and mono-, di- or tri-phosphate esters. In such esters unless otherwise specified, any alkyl moiety present advantageously contains 1 to 18 carbon atoms, particularly 1 to 4 carbon atoms. Any aryl moiety present in such esters advantageously comprises a phenyl group. Any reference to any of the above compounds also includes a reference to a pharmaceutically acceptable salt thereof.

Examples of pharmaceutically acceptable salts of the compound of formula (I) and pharmaceutically acceptable derivatives thereof include base salts, e.g. derived an appropriate base, such as alkali metal (e.g. sodium), alkaline earth metal (e.g. magnesium) salts, ammonium and $NX^+_4$ (wherein X is $C_{1-4}$ alkyl).

The compounds according to the invention may be employed in combination with other therapeutic agents for the treatment of the above infections or conditions. Examples of such further therapeutic agents include agents that are effective for the treatment of HIV infections or associated conditions such as 3'-azido-3'-deoxythymidine (zidovudine), other 2',3'-dideoxynucleosides such as 2', 3'-dideoxycytidine, 2',3'-dideoxyadenosine and 2',3'-dideoxyinosine, carbovir, acyclic nucleosides (e.g. acyclovir), 2',3'-didehydrothymidine, interferons such as α-interferon, renal excretion inhibitors such as probenicid, nucleoside transport inhibitors such as dipyridamole, as well as immunomodulators such as interleukin II and granulocyte macrophage colony stimulating factors, phosphonoformic acid and soluble $CD_4$ and genetically engineered derivatives thereof. The component compounds of such combination therapy may be administered simultaneously, in either separate or combined formulations, or at different times, e.g. sequentially, such that a combined effect is achieved.

The compounds according to the invention, also referred to herein as active ingredients, may be administered for therapy by any suitable route including oral, rectal, nasal, topical (including buccal and sublingual), vaginal and parenteral (including subcutaneous, intramuscular, intravenous and intradermal. It will also be appreciated that the preferred route will vary with the condition and age of the recipient, the nature of the infection and the chosen active ingredient.

In general a suitable dose for each of the above named antiviral infections, e.g., HIV or HBV infections, is in the range of 3.0 to 120 mg per kilogram body weight of the recipient, e.g., a mammal such as a human, preferably in the range of 6 to 90 mg per kilogram body weight per day and most preferably in the range 15 to 60 mg per kilogram body weight per day. The desired dose is preferably presented as two, three, four, five, six or more sub-doses administered at appropriate intervals throughout the day. These sub-doses may be administered in unit dosage forms, for example, containing 10 to 1500 mg, preferably 20 to 1000 mg, and most preferably 50 to 700 mg of active ingredient per unit dosage form.

Ideally, the active ingredient should be administered to achieve peak plasma concentrations of the active compound of from about 1 to about 75 $\mu M$, preferably about 2 to 50 $\mu M$, most preferably about 3 to about 30 $\mu M$. This may be achieved, for example, by the intravenous injection of a 0.1 to 5% solution of the active ingredient, optionally in saline, or orally administered as a bolus containing about 1 to about 100 mg/kg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible for the active ingredient to be administered alone it is preferable to present it as a pharmaceutical formulation. The formulations of the present invention comprises at least one active ingredient, as defined above, together with one or more acceptable carriers thereof and optionally other therapeutic agents. Each carrier must be "acceptable" in the sense of being compatible with the other ingredients of the formulation and not injurious to the patient. Formulations include those suitable for oral, rectal, nasal, topical (including buccal and sublingual), vaginal or parenteral (including subcutaneous, intramuscular, intravenous and intradermal) adminstration. The formulations may conveniently be presented in unit dosage form and may be prepared by any methods well know in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, crossed-linked sodium carboxmethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention may be formulated as an ointment, cream, suspension, lotion, powder, solution, paste, gel, spray, aerosol or oil. Alternatively, a formulation may comprise a dressing such as a bandage or adhesive plaster impregnated with active ingredients and optionally one or more excipients or diluents. Carriers which may be used include e.g. polyhydric alcohols such as polyethylene glycols, propylene glycol or glycerol. Suitable excipients are those known in the art to be appropriate.

Formulations for rectal administration may be presented as a suppository with a suitable base comprising for example cocoa butter or a salicylate.

Formulations suitable for vaginal administration may be presented as pessaries, tampons, creams, gels pastes, foams or spray formulations containing in addition to the active ingredient such carriers as are known in the art to be appropriate.

Formulations suitable for parenteral administration include aqueous and non-aqueous isotonic sterile injections solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injections solutions and suspensions may be prepared from sterile powders, granules and tablets of the kind previously described.

Preferred unit dosage formulations are those containing a daily dose or unit, daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example, those suitable for oral administration may include such further agents as sweeteners, thickeners and flavouring agents.

The compounds according to the invention may also be presented for the use in the form of veterinary formulations, which may be prepared, for example, by methods that are conventional in the art.

The present invention further includes a process for the preparation of the compound of formula (I) and pharmaceutically acceptable derivatives thereof which comprises either:

(A) removing a protecting group from a compound of formula (II):

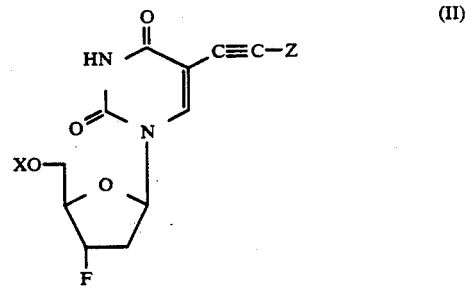

(wherein X represents hydrogen or a hydroxy protecting group and Z represents hydrogen or an ethynyl protecting group, providing at least one of X and Z represents a protecting group);

(B) reacting a compound of formula (III):

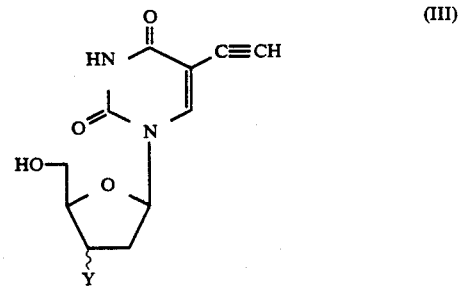

(wherein Y represents a precursor group for the fluoro group) with an agent or under conditions serving to convert the said precursor group to a fluoro group; or (C) reacting a pyrimidine base of formula (IV):

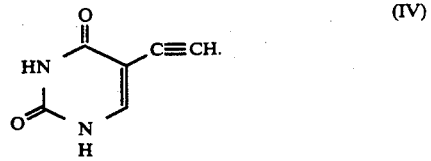

or a functional equivalent thereof, with a compound serving to introduce the desired ribofuranosyl ring at the 1-position of the pyrimidine base of formula (IV); and thereafter, or simultaneously therewith, effecting one or more of the following optional conversions:

(i) removing any remaining protecting groups;
(ii) when a compound of formula (I) is formed, converting it into a pharmaceutically acceptable derivative thereof;
(iii) when a pharmaceutically acceptable derivative of a compound of formula (I) is formed, converting the said derivative into a compound of formula (I), or a different derivative thereof.

In the above-described process according to the invention it will be appreciated that the starting compounds of formulae (II), (III) and (IV), as well as the above-mentioned agents and conditions, will be selected from those that are known in the art of nucleoside synthetic chemistry. For example as described in Nucleic Acid Chemistry: Improved New Synthetic Procedures, Methods and Techniques. Ed. L. B. Townsend and R. S. Tipson-Wiley Interscience (1978) and Nucleoside Analogues: Chemistry, Biology and Medical Applications, Ed. R. T. Walker, E. de Clercq and F. Eckstein, NATO Advanced Study Instituted, Plenum press (1979). Examples of such conversion procedures are described hereinafter for guidance and it will be understood that they can be modified in conventional manner depending on the desired compound of formula (I). In particular, where a conversion is described which would otherwise result in the undesired reaction of labile groups then such groups may be protected in conventional manner, with subsequent removal of the protecting groups after completion of the conversion.

In process (A), X may represent for example a hydroxy protecting group e.g. an ester grouping particularly $C_{1-6}$ alkanoyl (e.g. acetyl) or aroyl, (e.g. toluoyl), or an alkoxycarbonyl (e.g. methoxycarbonyl); or an ether group such as a trialkylsily group, e.g. t-butyldimethylsilyl or an aralkyl group e.g. triphenylmethyl. Such groups may be converted for example by hydrolysis to the desired hydroxy group or, by transesterification, of an ester group to an alternative ester group. A particularly preferred hydroxy protecting group is the p-toluoyl group which may be removed for example by treatment under basic conditions, e.g. with sodium methoxide/methanol, aqueous methylamine or ammonia. The above toluoyl derivative may be prepared by treating the appropriate parent compound with for example p-toluoyl chloride, in a base solvent such as pyridine.

Another preferred hydroxy protecting group is the acetyl group which may also be removed under basic conditions, e.g. as described above. The acetyl derivative may be prepared by treating the appropriate parent compound with for example, acetic anhydride in pyridine.

Examples of the protecting groups of the ethynyl group represented by Z in formula (II) include trialkylsilyl (e.g. trimethylsilyl) groups which may be removed by treatment under basic conditions using for example sodium methoxide/methanol.

The compounds of formula (II) may be prepared for example by the method described by Robins et al, Can.J.Chem. 60, 554 et seq (1982), e.g. by treating a corresponding compound in which the 5-position of the uracil base is substituted with a leaving group, for example halogen such as iodine and in which the 5'-hydroxy group is protected for example by an acyl group such as a p-toluoyl or acetyl group, with the appropriate protected alkynylene compound, such as trimethylsilylacetylene, with a palladium catalyst and another catalyst such as a copper (I) salt in the presence of an organic base, such as triethylamine, which also serves as a solvent, at an elevated temperature such as 50° C. to give the protected 5-alkynyl nucleoside. A preferred palladium catalyst is bis(triphenylphosphine) palladium dichloride and a preferred copper catalyst is cuprous iodide. The parent compound can readily be obtained by removal of any alkynyl protecting groups for example trialkylsilyl by treatment under basic conditions using for example sodium methoxide/methanol.

The starting material referred to above in which the 5-position of the uracil base is substituted with a halogen (particularly a chlorine, bromine or iodine) atom may be prepared for example by halogenating a corresponding uridine compound in which the 5-position is unsubstituted and in which the 5'-hydroxy group is blocked, for example by an acyl group such as p-toluoyl or acetyl group. Halogenation of the above starting material may be effected in conventional manner, for example iodination using iodine monochloride e.g. in methylene dichloride, or iodine in a solvent containing nitric acid, bromination using bromine e.g. in glacial acetic acid, or chlorination using a chlorine complex of iodobenzene, e.g. in glacial acetic acid.

The starting materials for the last-mentioned process, i.e. the 5'-hydroxy blocked uracil nucleoside may be prepared as described for example by G. Kowollik et al, J. Prakt. Chem. 1973. 315(5) 895-900 for the preparation of 2',3'-dideoxy-3'-fluorouridine and subsequent blocking of the 5'-hydroxy group in conventional manner, e.g. in the case of acyl blocking groups, by treatment with an appropriate acyl halide (e.g. chloride) or an anhydride as described above.

With regard to process (B), this may be effected for example by treatment of a compound of formula III in which Y represents a leaving group e.g. hydroxy or protected hydroxy such as mesyl or trifluorosulphonyl with an appropriate fluorinating agent such as hydrogen fluoride, potassium fluoride, potassium hydrogen fluoride diethylaminosulphurtrifluoride or tetra-n-butylammonium fluoride.

Process (C) may be effected for example by treating the pyrimidine base of formula (IV) or a salt or protected derivative thereof, with 3'-deoxy-3'-fluorothymidine for example in the presence of the appropriate pentosyl transferring enzyme or an organic catalyst such as trimethylsilyl or trifluoromethane sulphonate in a buffered aqueous solution.

The compound of formula (I) may be converted into a pharmaceutically acceptable ester thereof by reaction with an appropriate esterifying agent, e.g. an acid halide or anhydride. The compound of formula (I), including esters thereof, may be converted into pharmaceutically acceptable salts thereof in conventional manner, e.g. by treatment with an appropriate base. An ester or salt of a compound of formula (I) may be converted into the parent compound, e.g. by hydrolysis.

The following Examples are intended for illustration only and are not intended to limit the scope of the invention in any way. The term 'active ingredient' as used in the Examples means a compound of formula (I) or a pharmaceutically acceptable derivative thereof.

EXAMPLE 1 a) 2',3'-Dideoxy-3'-fluoro-5'-O-p-toluoyluridine p-Toluoyl chloride (freshly distilled, 325 mg, 2.10 mmol) was added to a solution of 2',3'-dideoxy-3'-fluorouridine (G. Kowollick et al, J. Prakt.Chem. 315(5), 895,1973) (440 mg, 1.91 mmol) in dry pyridine (10 ml). The solution was stirred at 50° for 1.5 hour, and then at 25° for 18 hours. The pyridine was evaporated and the residue dissolved in $CHCl_3$ (25 ml). This solution was extracted with 1M $H_2SO_4$ (5 ml), then $H_2O$ (2×10 ml), and dried $MgSO_4$. Evaporation of $CHCl_3$ left a colourless glass (0.72 g) which was chromatographed on silica gel. Elution with 2% MeOH-$CHCl_3$ gave the title product as white solid foam.

Yield - 0.66. 90% b) 2',3'-Dideoxy-3'-fluoro-5-iodo-5'-O-p-toluoyluridine

The product of Stage a) (200 mg, 0.574 mmol), iodine monochloride (139 mg, 0.861 nmol), and methylene chloride (0 ml) were refluxed for 2 hours. The solution was decolourised with a minimum of 2% aqueous NaHSO₃ (ca. 2 ml). The aqueous layer was separated and the organic layer washed with water (2×5 ml) and dried (MgSO₄). Evaporation of the solvent left a cream coloured solid foam identified as the title compound.

Yield - 0.25 g, 92% c) 2',3'-Dideoxy-3'-fluoro-5'-p-toluoyl-5-(trimethylsilylethynyl) uridine

The product of Stage b), (0.23 g, 0.485 mmol), cuprous iodide (10 mg), bis(triphenylphosphine) palladium (II) chloride (10 mg), trimethylsilylacetylene (0.145 g, 1.455 mmol) and dry triethylamine (15 ml) are stirred at 50° C. under a dry N₂ atmosphere for 3.0 hr. The cooled suspension is evaporated to dryness and the dark residue taken up in dichloromethane (20 ml). The solution is washed successively with 2% aqueous disodium ethylenediaminetetraacetic acid (2×30 ml), water 30 ml, dried (MgSO₄) and evaporated to give the title compound which is recrystallized from ethanol.

d) 2',3'-Dideoxy-5-ethynyl-3'-fluorouridine

A solution of the product of Stage c), in 0.2M sodium methoxide in methanol (freshly prepared from sodium and methanol) is stirred at room temperature for 3.0 hr. then neutralized by portionwise addition of Dowex 50 (H+) ion exchange resin. The resin is filtered off and washed well with methanol. The filtrate is evaporated to dryness and the residue partitioned between water and ether. The aqueous layer is washed with ether then evaporated to dryness, the residue triturated with ethanol and the solid filtered and washed with ether to give the title compound.

EXAMPLE 2 a) 2',3'-Dideoxy-3'-fluoro-5'-O-p-toluoyluridine

To a stirred solution of 2',3'-dideoxy-3'-fluorouridine (1 g, 4.34 mmoles) in dry pyridine (25 ml) at 0° C. was slowly added freshly distilled p-toluoyl chloride (0.63 ml, 4.78 mmoles). After the addition was complete, the mixture was stirred at 50° C. for 1.5 hrs., cooled and the solvent removed under reduced pressure. The residue was dissolved in chloroform (35 ml) and the solution extracted with 1M sulphuric acid (2×20 ml), water (2×30 ml) and dried (sodium sulphate). Evaporation of the solvent and purification of the residue by silica column chromatography eluting with 5% MeOH/CH₂Cl₂ afforded the title compound.

Yield: 1.2 g, 80% b) 2',3'-Dideoxy-3'-fluoro-5-iodo-5'-O-p-toluoyluridine

A solution of the product of Stage a), (3 g, 8.61 mmoles) and iodine monochloride (2.1 g, 12.92 mmoles) in methylene chloride (60 ml) was heated at reflux for 2 hrs. The cooled reaction mixture was diluted with methylene chloride (60 ml), washed with the minimum quantity of 2% aqueous sodium sulphite solution to achieve decolorisation, water (2×70 ml) and dried (sodium sulphate). Evaporation of the solvent afforded the title compound as a white foam.

Yield: 4 g, 98% c) 2',3'-Dideoxy-3'-fluoro-5'-O-p-toluoyl-5-(trimethylsilylethynyl) uridine

A solution of the product of Stage b), (0.8 g, 1.69 mmoles), bis(triphenylphosphine) palladium (II) chloride (25 mg) and copper (I) iodide (25 mg) in dry triethylamine (40ml) and N,N-dimethylformamide (3 ml) was degassed thoroughly with nitrogen. (Trimethylsilyl) acetylene (0.47 ml, 3.37 mmoles) was added and the mixture stirred under N₂ at 50° for 8 hours. The solvent was removed under reduced pressure, the residue dissolved in methylene chloride (40 ml) and the solution washed with 2% aqueous disodium EDTA solution (4 ml), water (50 ml) and dried (sodium sulphate). Evaporation of the solvent and purification of the residue by silica column chromatography eluting with 2% MeOH/CH₂Cl₂ afforded the title compound. Trituration with ether/hexane afforded analytically pure title compound as an off-white powder.

Yield: 0.56 g, 74%

M.pt.=130° C.

Microanalysis: calculated C,59.49;H,5.63;N,6.30% found C,59.54;H,5.75;N,6.29% d) 2',3'-Dideoxy-5-ethynyl-3'-fluorouridine

The product of Stage c), (0.53 g, 1.18 mmoles) was dissolved in methanol (17ml) containing sodium methoxide (from 0.027g, 1.18mmoles of sodium metal) and the solution left standing at ambient temperature for 7 hours. The mixture was then neutralised with Dowex 50 (H+) resin, filtered and evaporated to dryness. The final residue was triturated with ether (2×7 ml) and recrystallised from ethanol to give the title compound.

Yield=0.144 g, 50%

M.pt=225°-6° C.

Microanalysis: calculated C,51.99;H,4.33;N,11.02% found C,52.14;H,4.48;N,10.98%

EXAMPLE 3 a) 5'-O-Acetyl-2',3'-dideoxy-3'-fluorouridine

Acetic anhydride (1.2 ml, 13 mmol) was added to a solution of 2',3'-dideoxy-3'-fluorouridine (1 g, 4.34 mmol) in dry pyridine (10 ml) and the mixture was stirred at room temperature for 24 hours. Ethanol (2 ml) was added and the mixture was evaporated to dryness. Residual pyridine was removed by coevaporation with portions of ethanol and the final residue purified by silica gel column chromatography eluting with 5% MeOH/CH₂Cl₂ to give the title compound which was isolated following trituration with ether.

Yield: 0.91 g, 77% b) 5'-O-Acetyl-2',3'-dideoxy-3'-fluoro-5-iodouridine

Iodine monochloride (0.3 ml, 6 mmol) and the product of stage a) (0.91 g, 3.34 mmol) were combined in dichloromethane (10 ml) and the mixture heated at reflux for 3 hours. On cooling to room temperature, the solution was diluted with dichloromethane (20 ml) and washed with the minimum volume of 2% aqueous sodium sulphite solution to achieve decolorisation, water (2×30 ml) and dried (Na₂SO₄). Evaporation of the solvent afforded the title compound as an off-white foam.

Yield: 1.27 g, 96% c)

5'-O-Acetyl-2',3'-dideoxy-3'-fluoro-5-(trimethylsilylethynyl)uridine

A mixture of the product of stage b) (0.7 g, 1.76 mmol), bis-triphenylphosphine palladium (II) chloride (0.036 g) and copper (I) iodide (36 mg) in redistilled triethylamine (35 ml) was degassed with oxygen-free nitrogen. Trimethylsilylacetylene (0.49 ml, 3.52 mmol) was added and the mixture was stirred under a nitrogen atmosphere at room temperature for 60 hours. The solvent was evaporated, the residue dissolved in dichloromethane (30 ml) and the solution washed with a 2% aqueous solution disodium EDTA (2×30 ml), water (40 ml) and dried ($Na_2SO_4$). Evaporation of the solvent and purification of the residue by silica gel column chromatography eluting with 40% ethyl acetate/toluene afforded the title compound as a foam.

Yield=0.37 g, 58% d) 2',3'-Dideoxy-5-ethynyl-3'-fluorouridine

The product of stage c) (0.33 g, 0.9 mmol) was added to a solution of sodium methoxide (from 0.021 g, 0.9 mmol of sodium metal) in dry methanol (8 ml) and the mixture stirred at room temperature for 5 hours. The solution was neutralised with Dowex 50 ($H^+$) resin, the resin filtered and washed with methanol (2×4 ml) and the combined filtrate and washings evaporated to dryness. The residue was washed with ether (2×5 ml) and recrystallised from acetonitrile to give pale yellow crystals of the title compound.

Yield=0.17 g, 74%

M.pt. 224.5° C.

Microanalysis calculated C, 51.99; H, 4.33; N, 11.02% found C, 51.87; H, 4.40; N, 10.90%

EXAMPLE 4 a)

2',3'-Dideoxy-5'-O-(N-fluorenylmethoxy-carbonyl-L-isoleucinyl)-3'-fluorouridine

N,N'-Dicyclohexylcarbodiimide (0.57 g, 2.8 mmol) and N-fluorenylmethoxycarbonyl-L-isoleucine (1 g, 2.8 mmol) were combined in dry methylene chloride (15 ml) and the mixture was stirred for 30 minutes at room temperature. The precipitated N,N'-dicyclohexylurea was filtered, washed with methylene chloride (2×5 ml) and to the combined filtrate and washings was added a solution of 2',3'-dideoxy-5-ethynyl-3'-fluorouridine (0.3 g, 1.18 mmol) and N,N-dimethylaminopyridine (0.087 g, 0.72 mmol) in dry dimethylformamide (5 ml). The mixture was stirred for 24 hours at room temperature and a further quantity of N,N'-dicyclohexylurea was filtered. The filtrate was evaporated to dryness and the residue purified by column chromatography eluting with 5%–15% acetone/methylene chloride to give a residue (0.64 g) which was further purified by addition of methylene chloride, filtration and evaporation to give the title compound.

Yield=0.57 g, 82% b)

2',3'-Dideoxy-5-ethynyl-3'-fluoro-5'-O-L-isoleucinyluridine

A 20% solution of piperidine in dry dimethylformamide (5 ml) was added to 2',3'-dideoxy-5-ethynyl-5'-O-(N-fluorenylmethoxycarbonyl-L-isoleucinyl)-3'-fluorouridine (0.57 g, 0.96 mmol) and after 4 minutes at room temperature, the solvents were evaporated rapidly under high vacuum with minimal heating. Trituration of the residue with several portions of ether afforded a crop of the title compound containing ~5% of N,N'-dicyclohexylurea.

Yield=0.145 g, 41%

M.pt. 98°–100° C.

Microanalysis calculated C, 55.61; H, 5.99; N, 11.445 found C, 55.70; H, 6.32; N, 11.10%

EXAMPLE 5

5'-O-Acetyl-2',3'-dideoxy-5-ethynyl-3'-fluorouridine

To a stirred solution of 2',3'-dideoxy-5-ethynyl-3'-fluorouridine (1.106 g 0.4 mmol) in dry pyridine (5 ml) at 0° C. was added acetic anhydride (0.05 ml, 0.48 mmol) and stirring maintained at 0° C. for 1.5 hours. After stirring at room temperature for 24 hours, a further aliquot of acetic anhydride (0.02 ml, 0.2 mmol) was added and the mixture stirred at room temperature for 3 hours. After quenching with methanol (1 ml) the solvent was removed by evaporation under reduced pressure and co-evaporated with portions of ethanol (2×30 ml). The residue was recrystallised from ethanol to give a white crystalline solid.

Yield=0.079 g, (64%)

M.pt. 160°–161° C.

Microanalysis calculated C, 52.70; H, 4.392; N, 9.46% found C, 52.43; H, 4.39; N, 9.20%

EXAMPLE 6

2',3'-Dideoxy-5-ethynyl-3'-fluoro-5'-O-(trimethylacetyl)uridine 0.2 hydrate

To a stirred solution of 2',3'-dodeoxy-5-ethynyl-3'-fluorouridine (0.106 g 0.4 mmol) in dry pyridine (5 ml) at 0° C. was added trimethylacetyl chloride (0.06 ml, 0.48 mmol) and stirring continued at 0° C. for 1.5 hours. After stirring at room temperature for 24 hours, a further aliquot of the acid chloride (0.03 ml, 0.24 mmol) was added and stirring maintained for a further 3 hours. After quenching with methanol (3 ml), the solvent was removed by evaporation under reduced pressure and co-evaporated with several portions of ethanol (2×30 ml) and the resulting oil was chromatrographed on a silica gel column eluting with 5% $MeOH/CH_2Cl_2$. The appropriate fractions were combined and evaporated to dryness and the residue was recrystallised twice from ethanol to give the chromatographically pure title product.

Yield=0.063 g, (45%)

M.pt. 182°–185° C.

Microanalysis for 0.2 hydrate calculated C=56,21; H=5.68; N=8.20% found C=55.96; H=5.57; N=8.01%

EXAMPLE 7

Tablet Formulations

The following formulations A and B are prepared by wet granulation of the ingredients with a solution of povidone, followed by addition of magnesium stearate and compression.

|  | mg/tablet | mg/tablet |
| --- | --- | --- |
| Formulation A |  |  |
| (a) Active ingredient | 250 | 250 |
| (b) Lactose B.P. | 210 | 26 |
| (c) Povidone B.P. | 15 | 9 |
| (d) Sodium Starch Glycollate | 20 | 12 |

-continued

|  | mg/tablet | mg/tablet |
|---|---|---|
| (e) Magnesium Stearate | 5 | 3 |
|  | 500 | 300 |
| Formulation B |  |  |
| (a) Active ingredient | 250 | 250 |
| (b) Lactose | 150 | — |
| (c) Avicel PH 101 | 60 | 26 |
| (d) Povidone B.P. | 15 | 9 |
| (e) Sodium Starch Glycollate | 20 | 12 |
| (f) Magnesium Stearate | 5 | 3 |
|  | 500 | 300 |
| Formulation C |  |  |
| Active ingredient | 100 |  |
| Lactose | 200 |  |
| Starch | 50 |  |
| Povidone | 5 |  |
| Magnesium stearate | 4 |  |
|  | 359 |  |

The following formulations, D and E, are prepared by direct compression of the admixed ingredients.

|  | mg/capsule |
|---|---|
| Formulation D |  |
| Active Ingredient | 250 |
| Pregelatinised Starch NF15 | 150 |
|  | 400 |
| Formulation E |  |
| Active Ingredient | 250 |
| Lactose | 150 |
| Avicel | 100 |
|  | 500 |

Formulation F (Controlled Release Formulation)

The formulation is prepared by wet granulation of the following ingredients with a solution of povidone followed by the addition of magnesium stearate and compression.

|  | mg/tablet |
|---|---|
| (a) Active Ingredient | 500 |
| (b) Hydroxypropylmethylcellulose (Methocel K4M Premium) | 112 |
| (c) Lactose B.P. | 53 |
| (d) Povidone B.P.C. | 28 |
| (e) Magnesium Stearate | 7 |
|  | 700 |

Drug release takes place over a period of about 6-8 hours and is complete after 12 hours.

EXAMPLE 8

Capsule Formulations

Formulation A

A capsule formulation is prepared by admixing the ingredients of Formulation D in Example 4 above and filling into a two-part hard gelatin capsule.

| Formulation B | mg/capsule |
|---|---|
| (a) Active ingredient | 250 |
| (b) Lactose B.P. | 143 |
| (c) Sodium starch Glycollate | 25 |
| (d) Magnesium Stearate | 2 |
|  | 420 |

Capsules are prepared by admixing the above ingredients and filling into a two-part hard gelatin capsule.

| Formulation C | mg/capsule |
|---|---|
| (a) Active ingredient | 250 |
| (b) Macrogol 4000 BP | 350 |
|  | 600 |

Capsules are prepared by melting the Macrogol 4000 BP, dispersing the active ingredient in the melt and filling the melt into a two-part hard gelatin capsule.

| Formulation D | mg/capsule |
|---|---|
| Active ingredient | 250 |
| Lecithin | 100 |
| Arachis Oil | 100 |
|  | 450 |

Capsules are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients (a), (b) and (c) using an extruder, followed by spheronisation of the extrudate and drying. The dried pellets are then coated with release-controlling membrane (d) and filled into a two-piece, hard gelatin capsule.

|  | mg/capsule |
|---|---|
| (a) Active Ingredient | 250 |
| (b) Microcrystalline Cellulose | 125 |
| (c) Lactose BP | 125 |
| (d) Ethyl Cellulose | 13 |
|  | 513 |

EXAMPLE 9

Injectable Formulation

| Formulation A. |  |
|---|---|
| Active ingredient | 0.200 g |
| Hydrochloric acid solution, 0.1 M | q.s. to pH 4.0 to 7.0 |
| Sodium hydroxide solution, 0.1 M | q.s. to pH 4.0 to 7.0 |
| Sterile water | q.s. to 10 ml |

The active ingredient is dissolved in most of the water (35°–40° C.) and the pH adjusted to between 4.0 and 7.0 with the hydrochloric acid or the sodium hydroxide as appropriate. The batch is then made up to volume with the water and filtered through a sterile micropore filter into a sterile 10 ml amber glass vial (type 1) and sealed with sterile closures and overseals.

| Formulation B. |  |
|---|---|
| Active ingredient | 0.125 g |
| Sterile, pyrogen-free, pH 7 phosphate buffer | q.s. to 25 ml |

EXAMPLE 10

Intramuscular injection

| Active Ingredient | 0.20 g |
|---|---|
| Benzyl Alcohol | 0.10 g |
| Glycofurol 75 | 1.45 g |
| Water for Injection   q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml amber glass vials (type 1).

EXAMPLE 11

Syrup

| | |
|---|---|
| Active ingredient | 0.25 g |
| Sorbitol Solution | 1.50 g |
| Glycerol | 2.00 g |
| Sodium Benzoate | 0.005 g |
| Flavour, Peach 17.42.3169 | 0.0125 ml |
| Purified Water q.s. to | 5.00 ml |

The active ingredient is dissolved in a mixture of the glycerol and most of the purified water. An aqueous solution of the sodium benzoate is then added to the solution, followed by addition of the sorbitol solution and finally the flavour. The volume is made up with purified water and mixed well.

EXAMPLE 12

Suppository

| | mg/suppository |
|---|---|
| Active Ingredient | 250 |
| Hard Fat, BP (Witepsol H15 - Dynamit Nobel) | 1770 |
| | 2020 |

One-fifth of the Witepsol H15 is melted in a steam-jacketed pan at 45° C. maximum. The active ingredient is sifted through a 200 μm sieve and added to the molten base with mixing, using a silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 μm stainless steel screen and, with continuous stirring, is allowed to cool to 40° C. At a temperature of 38° C. to 40° C., 2.02 g of the mixture is filled into suitable, 2 ml plastic moulds. The suppositories are allowed to cool to room temperature.

EXAMPLE 13

Pessaries

| | mg/pessary |
|---|---|
| Active ingredient | 250 |
| Anhydrate Dextrose | 380 |
| Potato Starch | 363 |
| Magnesium Stearate | 7 |
| | 1000 |

The above ingredients are mixed directly and pessaries prepared by direct compression of the resulting mixture.

EXAMPLE 14

Antiviral and Toxicity Testing

Antiviral activity against the Human Immunodeficiency Virus (HIV) was determined by measuring the ability of the compound to reverse the cytopathic effect of HIV infection. This was determined by a quantitative assessment of cell growth monitored at the fifth day post infection by a uptake test. Subconfluent (20–40,000 cells/well) human T lymphocyte cell line MT4 cells infected with HIV were grown in 96-well microtiter dishes and exposed to different dilutions of drug. After 5 days, the dye intake test was performed on drug treated cultures and on HIV infected and mock infected MT4 cells. Under the conditions of the test, HIV infection caused extensive cytopathic effect and prevented cell growth by >80%. The antiviral effect of a drug is reported as an IC-50, i.e. as the inhibitory concentration that would protect 50% of the cells from cell killing, measured as 50% of that cell growth determined for uninfected MT4 cell controls.

Cell toxicity was assessed in a cell growth inhibition assay on uninfected MT4 cells or on vero cells in a 96-well microtiter dish. Identical cell numbers of uninfected cells were exposed to different dilutions of drug and cell viability determined daily on replicate cultures using uptake of MTT. The concentration required for a 50% inhibition of cell viability at 5 days is termed CCID-50.

| Compound | $IC_{50}HIV$ | $CCID_{50}$ |
|---|---|---|
| 2',3'-dideoxy-5-ethynyl-3'-fluorouridine | 8.9 μM | 224 μM(MT4 cells) |
| 2',3'-dideoxy-5-ethynyl-3'-fluorouridine | — | 464 μM(Vero cells) |

We claim:

1. A pharmaceutically acceptable carboxylic acid ester of the compound 2',3'-dideoxy-5-ethynyl-3'-fluorouridine or a pharmaceutically acceptable salt of such ester, the non-carbonyl moiety of said ester or salt thereof selected from straight or branched chain alkyl, the alkyl moiety present containing 1 to 4 carbon atoms.

2. A pharmaceutically acceptable alkylsulphonate or aralkylsulphonate ester of the compound 2',3'-dideoxy-5-ethynyl-3'-fluorouridine or a pharmaceutically acceptable salt of said ester, said alkyl group containing 1 to 18 carbon atoms and said aryl group being phenyl.

3. A pharmaceutically acceptable 5'-mono-, 5'-di- or 5'-tri-phosphate ester of the compound 2',3'-dideoxy-5-ethynyl-3'-fluorouridine or a pharmaceutically acceptable salt of said ester.

4. A pharmaceutically acceptable L-valyl amino acid ester of the compound 2',3'-dideoxy-5-ethynyl-3'-fluorouridine or a pharmaceutically acceptable salt of said ester.

5. A pharmaceutically acceptable L-isoleucyl amino acid ester of the compound 2',3'-dideoxy-5-ethynyl-3'-fluorouridine or a pharmaceutically acceptable salt of said ester.

* * * * *